(12) United States Patent
Palreddy et al.

(10) Patent No.: US 9,242,112 B2
(45) Date of Patent: Jan. 26, 2016

(54) DATA MANIPULATION FOLLOWING DELIVERY OF A CARDIAC STIMULUS IN AN IMPLANTABLE CARDIAC STIMULUS DEVICE

(71) Applicant: Cameron Health, Inc., San Clemente, CA (US)

(72) Inventors: Surekha Palreddy, Maplewood, MN (US); Venugopal Allavatam, San Clemente, CA (US)

(73) Assignee: CAMERON HEALTH, INC., St. Paul, MN (US)

( * ) Notice: Subject to any disclaimer, the term of this patent is extended or adjusted under 35 U.S.C. 154(b) by 0 days.

(21) Appl. No.: 14/184,758

(22) Filed: Feb. 20, 2014

(65) Prior Publication Data
US 2014/0172032 A1    Jun. 19, 2014

Related U.S. Application Data

(60) Continuation of application No. 13/898,738, filed on May 21, 2013, now Pat. No. 8,700,152, which is a division of application No. 12/355,552, filed on Jan. 16, 2009, now Pat. No. 8,494,630.

(60) Provisional application No. 61/022,265, filed on Jan. 18, 2008.

(51) Int. Cl.
*A61N 1/05* (2006.01)
*A61N 1/39* (2006.01)
(Continued)

(52) U.S. Cl.
CPC ............ *A61N 1/3943* (2013.01); *A61B 5/0468* (2013.01); *A61N 1/3704* (2013.01); *A61N 1/3987* (2013.01); *A61N 1/0504* (2013.01); *A61N 1/3756* (2013.01); *A61N 1/3925* (2013.01)

(58) Field of Classification Search
CPC . A61N 1/3943; A61N 1/3987; A61N 1/3704; A61N 1/3756; A61N 1/0504; A61N 1/3925; A61B 5/0468

USPC .......... 607/4, 5, 9, 17; 600/509, 510, 515–518
See application file for complete search history.

(56) References Cited

U.S. PATENT DOCUMENTS

| | | |
|---|---|---|
| 4,184,493 A | 1/1980 | Langer et al. |
| 4,300,567 A | 11/1981 | Kolenik et al. |

(Continued)

FOREIGN PATENT DOCUMENTS

| | | |
|---|---|---|
| EP | 0554208 A2 | 8/1993 |
| WO | WO-0243802 A2 | 6/2002 |

(Continued)

OTHER PUBLICATIONS

U.S. Appl. No. 12/355,552, Advisory Action mailed Jun. 5, 2012, 5 pgs.

(Continued)

*Primary Examiner* — Rex R Holmes
(74) *Attorney, Agent, or Firm* — Seager, Tufte & Wickhem LLP (57) ABSTRACT

Methods of cardiac rhythm analysis in an implantable cardiac stimulus device, and devices configured for such methods. In an illustrative embodiment, certain data relating to cardiac event rate or amplitude is modified following delivery of a cardiac stimulus. In another embodiment, cardiac rhythm analysis is performed using one of plural states, with the plural states using different criteria, such as a detection threshold, to detect cardiac events in a sensed signal. Following delivery of a cardiac stimulus, data is manipulated to force the analysis into one of the states, where stimulus is delivered, in the illustrative embodiment, only after a different state is invoked. Implantable devices incorporating operational circuitry for performing such methods are also included in other illustrative embodiments.

9 Claims, 8 Drawing Sheets

(51) Int. Cl.
  *A61B 5/0468* (2006.01)
  *A61N 1/37* (2006.01)
  *A61N 1/375* (2006.01)

(56) References Cited

U.S. PATENT DOCUMENTS

| | | | |
|---|---|---|---|
| 4,407,288 A | 10/1983 | Langer et al. |
| 4,450,527 A | 5/1984 | Sramek |
| 4,457,315 A | 7/1984 | Bennish |
| 4,589,420 A | 5/1986 | Adams et al. |
| 4,595,009 A | 6/1986 | Leinders |
| 4,679,144 A | 7/1987 | Cox et al. |
| 4,693,253 A | 9/1987 | Adams |
| 4,750,494 A | 6/1988 | King |
| 4,779,617 A | 10/1988 | Whigham |
| 4,979,110 A | 12/1990 | Albrecht et al. |
| 4,989,602 A | 2/1991 | Sholder et al. |
| 5,000,189 A | 3/1991 | Throne et al. |
| 5,105,810 A | 4/1992 | Collins et al. |
| 5,184,616 A | 2/1993 | Weiss |
| 5,193,535 A | 3/1993 | Bardy et al. |
| 5,215,098 A | 6/1993 | Steinhaus et al. |
| 5,217,021 A | 6/1993 | Steinhaus et al. |
| 5,271,411 A | 12/1993 | Ripley et al. |
| 5,280,792 A | 1/1994 | Leong et al. |
| 5,299,119 A | 3/1994 | Kraf et al. |
| 5,313,953 A | 5/1994 | Yomtov et al. |
| 5,331,966 A | 7/1994 | Bennett et al. |
| 5,342,402 A | 8/1994 | Olson et al. |
| 5,342,407 A | 8/1994 | Dahl et al. |
| 5,351,686 A | 10/1994 | Steuer et al. |
| 5,376,104 A | 12/1994 | Sakai et al. |
| 5,423,326 A | 6/1995 | Wang et al. |
| 5,447,519 A | 9/1995 | Peterson |
| 5,522,852 A | 6/1996 | White et al. |
| 5,534,019 A | 7/1996 | Paspa |
| 5,545,186 A | 8/1996 | Olson et al. |
| 5,558,098 A | 9/1996 | Fain |
| 5,607,455 A | 3/1997 | Armstrong |
| 5,658,317 A | 8/1997 | Haefner et al. |
| 5,709,215 A | 1/1998 | Perttu et al. |
| 5,817,134 A | 10/1998 | Greenhut |
| 5,827,197 A | 10/1998 | Bocek et al. |
| 5,857,977 A | 1/1999 | Caswell et al. |
| 5,891,048 A | 4/1999 | Nigam et al. |
| 5,991,657 A | 11/1999 | Kim |
| 6,029,086 A | 2/2000 | Kim et al. |
| 6,041,251 A | 3/2000 | Kim et al. |
| 6,047,210 A | 4/2000 | Kim et al. |
| 6,052,617 A | 4/2000 | Kim |
| 6,058,328 A | 5/2000 | Levine et al. |
| 6,095,987 A | 8/2000 | Shmulewitz et al. |
| 6,115,628 A | 9/2000 | Stadler et al. |
| 6,144,879 A | 11/2000 | Gray |
| 6,148,230 A | 11/2000 | Kenknight |
| 6,223,078 B1 | 4/2001 | Marcovecchio |
| 6,230,055 B1 | 5/2001 | Sun et al. |
| 6,236,882 B1 | 5/2001 | Lee et al. |
| 6,240,313 B1 | 5/2001 | Esler |
| 6,266,554 B1 | 7/2001 | Hsu et al. |
| 6,280,462 B1 | 8/2001 | Hauser et al. |
| 6,308,095 B1 | 10/2001 | Hsu et al. |
| 6,334,071 B1 | 12/2001 | Lu |
| 6,377,844 B1 | 4/2002 | Graen |
| 6,381,493 B1 | 4/2002 | Stadler et al. |
| 6,393,316 B1 | 5/2002 | Gillberg et al. |
| 6,397,100 B2 | 5/2002 | Stadler et al. |
| 6,411,844 B1 | 6/2002 | Kroll et al. |
| 6,438,410 B2 | 8/2002 | Hsu et al. |
| 6,493,579 B1 | 12/2002 | Gilkerson et al. |
| 6,493,584 B1 | 12/2002 | Lu |
| 6,499,503 B2 | 12/2002 | Coscarella |
| 6,505,068 B2 | 1/2003 | Bonnet et al. |
| 6,516,225 B1 | 2/2003 | Florio |
| 6,561,984 B1 | 5/2003 | Turcott |
| 6,567,691 B1 | 5/2003 | Stadler |
| 6,574,505 B1 | 6/2003 | Warren |
| 6,575,912 B1 | 6/2003 | Turcott |
| 6,587,720 B2 | 7/2003 | Hsu et al. |
| 6,625,490 B1 | 9/2003 | McClure et al. |
| 6,643,549 B1 | 11/2003 | Bradley et al. |
| 6,647,292 B1 | 11/2003 | Bardy et al. |
| 6,684,100 B1 | 1/2004 | Sweeney et al. |
| 6,699,200 B2 | 3/2004 | Cao et al. |
| 6,708,058 B2 | 3/2004 | Kim et al. |
| 6,708,062 B2 | 3/2004 | Ericksen et al. |
| 6,721,597 B1 | 4/2004 | Bardy et al. |
| 6,728,572 B2 | 4/2004 | Hsu et al. |
| 6,731,978 B2 | 5/2004 | Olson et al. |
| 6,745,068 B2 | 6/2004 | Koyrakh et al. |
| 6,754,528 B2 | 6/2004 | Bardy et al. |
| 6,889,079 B2 | 5/2005 | Bocek et al. |
| 6,892,092 B2 | 5/2005 | Palreddy et al. |
| 6,909,916 B2 | 6/2005 | Spinelli et al. |
| 6,950,702 B2 | 9/2005 | Sweeney |
| 6,988,003 B2 | 1/2006 | Bardy et al. |
| 7,016,730 B2 | 3/2006 | Ternes |
| 7,020,523 B1 | 3/2006 | Lu et al. |
| 7,027,856 B2 | 4/2006 | Zhou et al. |
| 7,027,858 B2 | 4/2006 | Cao et al. |
| 7,027,862 B2 | 4/2006 | Dahl et al. |
| 7,031,764 B2 | 4/2006 | Schwartz et al. |
| 7,062,314 B2 | 6/2006 | Zhu et al. |
| 7,062,315 B2 | 6/2006 | Koyrakh et al. |
| 7,062,322 B2 | 6/2006 | Stadler et al. |
| 7,076,289 B2 | 7/2006 | Sakar et al. |
| 7,085,599 B2 | 8/2006 | Kim et al. |
| 7,117,035 B2 | 10/2006 | Wagner et al. |
| 7,130,689 B1 | 10/2006 | Turcott |
| 7,149,575 B2 | 12/2006 | Ostroff et al. |
| 7,162,301 B2 | 1/2007 | Kim et al. |
| 7,167,747 B2 | 1/2007 | Gunderson et al. |
| 7,181,281 B1 | 2/2007 | Kroll |
| 7,184,815 B2 | 2/2007 | Kim et al. |
| 7,184,818 B2 | 2/2007 | Kim et al. |
| 7,191,004 B2 | 3/2007 | Kim et al. |
| 7,194,302 B2 | 3/2007 | Bardy et al. |
| 7,218,966 B2 | 5/2007 | Haefner et al. |
| 7,236,819 B2 | 6/2007 | Brockway et al. |
| 7,248,921 B2 | 7/2007 | Palreddy et al. |
| 7,266,409 B2 | 9/2007 | Gunderson |
| 7,283,863 B2 | 10/2007 | Gunderson et al. |
| 7,302,294 B2 | 11/2007 | Kamath et al. |
| 7,330,757 B2 | 2/2008 | Ostroff et al. |
| 7,346,392 B2 | 3/2008 | Kenknight |
| 7,376,458 B2 | 5/2008 | Palreddy et al. |
| 7,379,772 B2 | 5/2008 | Bardy et al. |
| 7,386,342 B1 | 6/2008 | Falkenberg et al. |
| 7,392,085 B2 | 6/2008 | Warren et al. |
| 7,444,182 B2 | 10/2008 | Ostroff et al. |
| 7,447,540 B1 | 11/2008 | Nabutovsky et al. |
| 7,467,009 B2 | 12/2008 | Palreddy et al. |
| 7,477,935 B2 | 1/2009 | Palreddy et al. |
| 7,496,408 B2 | 2/2009 | Ghanem et al. |
| 7,496,409 B2 | 2/2009 | Greenhut et al. |
| 7,499,750 B2 | 3/2009 | Haefner et al. |
| 7,522,959 B2 | 4/2009 | Hauser et al. |
| 7,546,159 B1 | 6/2009 | Nabutovsky et al. |
| 7,555,335 B2 | 6/2009 | Kamath et al. |
| 7,559,900 B2 | 7/2009 | Gillberg |
| 7,567,835 B2 | 7/2009 | Gunderson et al. |
| 7,570,997 B2 | 8/2009 | Lovett et al. |
| 7,593,771 B2 | 9/2009 | Yonce et al. |
| 7,623,913 B2 | 11/2009 | Phillips |
| 7,623,916 B2 | 11/2009 | Julian |
| 7,655,014 B2 | 2/2010 | Ko et al. |
| 7,682,316 B2 | 3/2010 | Anderson et al. |
| 7,684,864 B2 | 3/2010 | Olson et al. |
| 7,715,906 B2 | 5/2010 | Krause et al. |
| 7,734,345 B2 | 6/2010 | Cinbis |
| 7,761,142 B2 | 7/2010 | Ghanem et al. |
| 7,774,049 B2 | 8/2010 | Ghanem et al. |
| 7,783,354 B2 | 8/2010 | Gunderson |
| 7,797,036 B2 | 9/2010 | Zhang et al. |

(56) References Cited

U.S. PATENT DOCUMENTS

| | | | |
|---|---|---|---|
| 7,865,233 B2 | 1/2011 | Haefner | |
| 7,894,894 B2 | 2/2011 | Stadler et al. | |
| 7,904,142 B2 | 3/2011 | Kim et al. | |
| 7,904,153 B2 | 3/2011 | Greenhut et al. | |
| 7,907,993 B2 | 3/2011 | Ghanem et al. | |
| 8,494,630 B2 | 7/2013 | Palreddy et al. | |
| 2003/0097153 A1* | 5/2003 | Bardy et al. | 607/5 |
| 2004/0215239 A1 | 10/2004 | Favet et al. | |
| 2004/0215240 A1 | 10/2004 | Lovett et al. | |
| 2004/0220628 A1 | 11/2004 | Wagner | |
| 2004/0230229 A1 | 11/2004 | Lovett et al. | |
| 2005/0107838 A1 | 5/2005 | Lovett et al. | |
| 2005/0131464 A1 | 6/2005 | Heinrich et al. | |
| 2005/0154421 A1 | 7/2005 | Ousdigian et al. | |
| 2005/0192505 A1* | 9/2005 | Ostroff et al. | 600/509 |
| 2006/0167502 A1 | 7/2006 | Haefner | |
| 2006/0167503 A1 | 7/2006 | Warren et al. | |
| 2006/0167504 A1 | 7/2006 | Warren et al. | |
| 2006/0224225 A1 | 10/2006 | Ransbury et al. | |
| 2006/0235476 A1 | 10/2006 | Gunderson et al. | |
| 2006/0241701 A1 | 10/2006 | Markowitz et al. | |
| 2007/0032829 A1 | 2/2007 | Ostroff | |
| 2007/0049975 A1 | 3/2007 | Cates et al. | |
| 2007/0049982 A1 | 3/2007 | Cao et al. | |
| 2007/0135847 A1 | 6/2007 | Kenknight | |
| 2007/0142736 A1 | 6/2007 | Cazares et al. | |
| 2007/0156190 A1 | 7/2007 | Cinbis | |
| 2007/0179539 A1 | 8/2007 | Degroot et al. | |
| 2007/0179540 A1 | 8/2007 | Stegemann et al. | |
| 2007/0232944 A1 | 10/2007 | Ghanem et al. | |
| 2007/0232945 A1 | 10/2007 | Kleckner et al. | |
| 2007/0232948 A1 | 10/2007 | Stadler et al. | |
| 2007/0233198 A1 | 10/2007 | Ghanem et al. | |
| 2007/0276445 A1 | 11/2007 | Sanghera et al. | |
| 2007/0276452 A1 | 11/2007 | Sanghera et al. | |
| 2008/0015647 A1 | 1/2008 | Palreddy et al. | |
| 2008/0077030 A1 | 3/2008 | Ostroff et al. | |
| 2008/0086174 A1 | 4/2008 | Libbus et al. | |
| 2008/0091242 A1 | 4/2008 | Kamath et al. | |
| 2008/0132965 A1 | 6/2008 | Ostroff et al. | |
| 2008/0161870 A1 | 7/2008 | Gunderson | |
| 2008/0172098 A1 | 7/2008 | Gunderson et al. | |
| 2008/0172100 A1 | 7/2008 | Sanghera et al. | |
| 2008/0183085 A1 | 7/2008 | Van Oort et al. | |
| 2008/0188901 A1 | 8/2008 | Sanghera et al. | |
| 2008/0215110 A1 | 9/2008 | Gunderson | |
| 2008/0221632 A1 | 9/2008 | Bardy et al. | |
| 2008/0228093 A1 | 9/2008 | Dong et al. | |
| 2008/0243200 A1 | 10/2008 | Scinicariello et al. | |
| 2008/0262559 A1 | 10/2008 | Zhang et al. | |
| 2008/0275516 A1 | 11/2008 | Ghanem et al. | |
| 2008/0275517 A1 | 11/2008 | Ghanem et al. | |
| 2008/0275519 A1 | 11/2008 | Ghanem et al. | |
| 2008/0275521 A1 | 11/2008 | Warren et al. | |
| 2009/0036788 A1 | 2/2009 | Nabutovsky et al. | |
| 2009/0043352 A1 | 2/2009 | Brooke et al. | |
| 2009/0054796 A1 | 2/2009 | Sanghera et al. | |
| 2009/0054938 A1 | 2/2009 | Ostroff et al. | |
| 2009/0093731 A1 | 4/2009 | Palreddy et al. | |
| 2009/0156957 A1 | 6/2009 | Linder et al. | |
| 2009/0157128 A1 | 6/2009 | Seim et al. | |
| 2009/0157132 A1 | 6/2009 | Linder et al. | |
| 2009/0157137 A1 | 6/2009 | Gilkerson et al. | |
| 2009/0187227 A1 | 7/2009 | Palreddy et al. | |
| 2009/0228057 A1 | 9/2009 | Allavatam et al. | |
| 2009/0240157 A1 | 9/2009 | Lian et al. | |
| 2009/0240300 A1 | 9/2009 | Lian et al. | |
| 2009/0259271 A1 | 10/2009 | Allavatam et al. | |
| 2010/0004713 A1 | 1/2010 | Warren et al. | |
| 2010/0094369 A1 | 4/2010 | Allavatam et al. | |
| 2010/0152798 A1 | 6/2010 | Sanghera et al. | |
| 2010/0152799 A1 | 6/2010 | Sanghera et al. | |
| 2010/0331904 A1 | 12/2010 | Warren et al. | |
| 2011/0098585 A1 | 4/2011 | Warren et al. | |
| 2011/0098775 A1 | 4/2011 | Allavatam et al. | |
| 2013/0253601 A1 | 9/2013 | Palreddy et al. | |

FOREIGN PATENT DOCUMENTS

| | | |
|---|---|---|
| WO | WO-02043802 A3 | 8/2002 |
| WO | WO-02043802 B1 | 10/2002 |
| WO | WO-2007140207 A1 | 12/2007 |

OTHER PUBLICATIONS

U.S. Appl. No. 12/355,552, Final Office Action mailed Mar. 20, 2012, 8 pgs.

U.S. Appl. No. 12/355,552, Non Final Office Action mailed Oct. 25, 2011, 8 pgs.

U.S. Appl. No. 12/355,552, Notice of Allowance mailed Mar. 25, 2013, 8 pgs.

U.S. Appl. No. 12/355,552, Response filed Jan. 13, 2012 to Non Final Office Action mailed Oct. 25, 2011, 10 pgs.

U.S. Appl. No. 12/355,552, Response filed May 21, 2012 to Final Office Action mailed Mar. 20, 2012, 10 pgs.

U.S. Appl. No. 12/355,552, Response filed Jun. 19, 2012 to Advisory Action mailed Jun. 5, 2012, 10 pgs.

U.S. Appl. No. 12/355,552, Response filed Oct. 7, 2011 to Restriction Requirement mailed Sep. 8, 2011, 10 pgs.

U.S. Appl. No. 12/355,552, Restriction Requirement mailed Sep. 8, 2011, 5 pgs.

U.S. Appl. No. 13/898,738, Notice of Allowance mailed Dec. 11, 2013, 9 pgs.

U.S. Appl. No. 13/898,738, Response filed Oct. 9, 2013 to Restriction Requirement mailed Sep. 9, 2013, 6 pgs.

U.S. Appl. No. 13/898,738, Restriction Requirement mailed Sep. 9, 2013, 7 pgs.

International Application Serial No. PCT/US2009/031352, International Preliminary Report on Patentability mailed Jul. 29, 2010, 7 pgs.

International Application Serial No. PCT/US2009/031352, International Search Report mailed May 6, 2009, 4 pgs.

International Application Serial No. PCT/US2009/031352, Written Opinion mailed May 6, 2009, 5 pgs.

Gunderson, et al., "An Algorithm to Predict Implantable Cardioverter-Defibrillator Lead Failure", JACC, vol. 44, No. 9,, (Nov. 2004), 1898-1902.

Olson, Walter H, et al., "Onset and Stability for Ventricular Tachyarrhythmia Detection in an Implantable Pacer-Cardioverter-Defibrillator", IEEE, (1987), 167-170.

Schuder, John C, "The Role of An Engineering Oriented Medical Research Group in Developing Improved Methods & Devices for Achieving Ventricular Defibrillation: The University of Missouri Experience", PACE, vol. 16, Part I, (Jan. 1993), 95-124.

Schwake, H., et al., "Komplikationen mit Sonden bei 340 Patienten mit einem implantierbaren Kardioverter/Defibrilator", Z Kardiol, vol. 88, No. 8, (1999), 559-565.

Swerdlow, C. D, et al., "Advanced ICD Troubleshooting: Part I", PACE, vol. 28, [Online]. Retrieved from the Internet: <http://www.medscape.com/viewarticle/520588_print>, (Jan. 9, 2006), 1322-1346.

Throne, Robert D, et al., "A Comparison of Four New Time-Domain Techniques for Discriminating Monomorphic Ventricular Tachycardia from Sinus Rhythm Using Ventricular Waveform Morphology", IEEE Transactions on Biomedical Engineering, vol. 38, No. 6, (Jun. 1991), 561-570.

* cited by examiner

DATA MANIPULATION FOLLOWING DELIVERY OF A CARDIAC STIMULUS IN AN IMPLANTABLE CARDIAC STIMULUS DEVICE

RELATED APPLICATIONS

The present application is a continuation of U.S. patent application Ser. No. 13/898,738, filed May 21, 2013, now U.S. Pat. No. 8,700,152, which is a divisional of U.S. patent application Ser. No. 12/355,552, filed Jan. 16, 2009, now U.S. Pat. No. 8,494,630, which claims the benefit of and priority to U.S. Provisional Patent Application No. 61/022,265, filed Jan. 18, 2008 and titled DATA MANIPULATION FOLLOWING DELIVERY OF A CARDIAC STIMULUS IN AN IMPLANTABLE CARDIAC STIMULUS DEVICE, the disclosures of which are incorporated herein by reference.

FIELD

The present invention relates to the field of the implantable cardiac stimulus device (ICSD). More particularly, the present invention relates to activity in an ICSD following delivery of a cardiac stimulus.

BACKGROUND

An implantable cardiac stimulus device (ICSD) is implanted into a patient in order to monitor and, if necessary, supplement or correct the electrical activity of the patient's heart. An ICSD may be configured to deliver pacing pulses to assist in regularizing heart function on an ongoing basis. An ICSD may also be configured to deliver defibrillation and/or cardioversion stimuli, which will typically be more energetic than pacing pulses. Some ICSDs can perform each of these functions in response to predetermined conditions.

With respect to the more energetic defibrillation and/or cardioversion stimuli, one goal of applying the stimulus is to change the state of heart function. For example, a tachyarrhythmia or fibrillation may be identified as malignant and can indicate therapy. One or more stimuli may be applied to convert the patient to normal sinus rhythm and/or a non-malignant rhythm. Some characteristics of the post-shock cardiac signal following successful conversion, for example, rate and morphology, may be quite different from those that occur prior to stimulus delivery. If conversion is not successful, however, the post-shock signal may have similar rate and morphology to the pre-shock signal. New and alternative methods and systems providing accurate detection of cardiac events following stimulus are desired.

SUMMARY

The present invention, in a first illustrative embodiment, includes a method of cardiac rhythm analysis in an implantable cardiac stimulus device. In the illustrative embodiment, certain stored data relating to cardiac event rate(s) or amplitude(s) is modified following delivery of a cardiac stimulus. In one example, cardiac event rate data is seeded following cardiac stimulus delivery to simulate a relatively low cardiac event rate. In another example, cardiac event amplitude data is seeded following cardiac stimulus delivery to simulate a relatively large amplitude cardiac signal. Implantable devices incorporating operational circuitry for performing such methods are also included in other illustrative embodiments.

In another embodiment, cardiac rhythm analysis is performed using one of plural states, with the plural states using different criteria, such as different detection threshold shapes, to detect cardiac events in a sensed signal. Following delivery of a cardiac stimulus, data is manipulated to force the analysis into one of the states, where stimulus is delivered, in the illustrative embodiment, only after a different state is invoked. For example, an illustrative device that is in a tachycardia state prior to therapy delivery has stored data manipulated to invoke a non-tachycardia state following therapy. Once "set" into the non-tachycardia state, cardiac signal analysis occurs and the device can reenter the tachycardia state if tachycardia is redetected.

This summary of the invention is provided to indicate certain features of some embodiments, and should not be misconstrued as indicating any feature or step is necessary or present in all embodiments.

DETAILED DESCRIPTION

The following detailed description should be read with reference to the drawings. The drawings, which are not necessarily to scale, depict illustrative embodiments and are not intended to limit the scope of the invention.

Figure 1A:
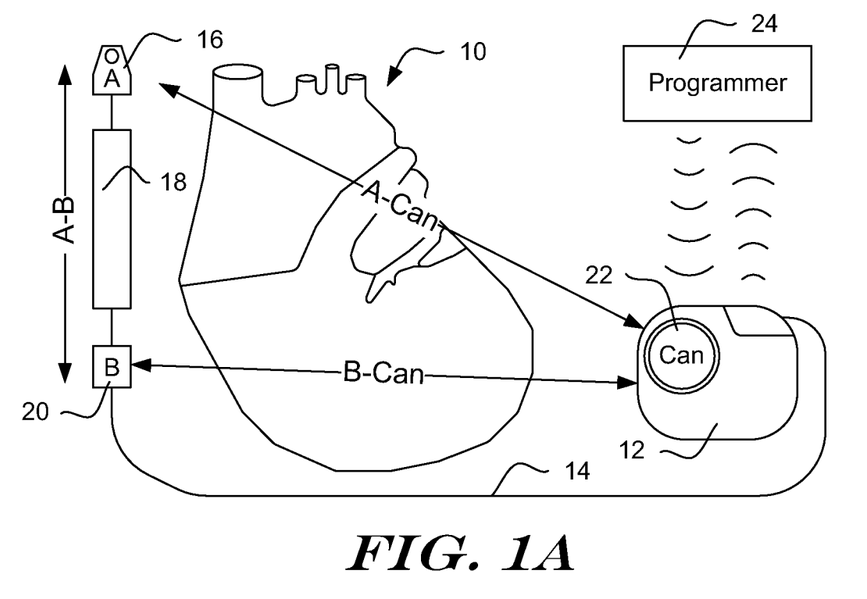
FIGS. 1A-1B show illustrative subcutaneous and transvenous cardiac stimulus systems.
Figure 1B:
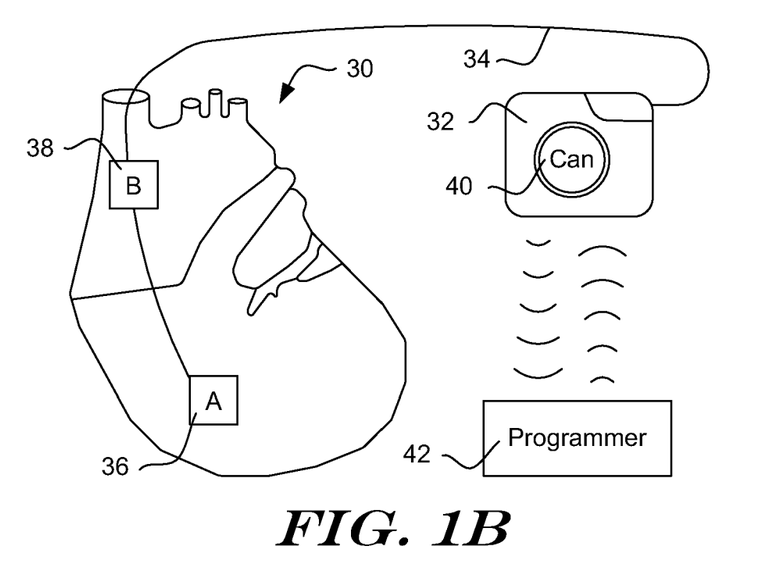

FIGS. 1A-1B, respectively, show subcutaneous and transvenous implanted cardiac stimulus systems relative to the heart. Referring to FIG. 1A, the patient's heart 10 is shown in relation to an implanted, subcutaneous cardiac stimulus system including a canister 12. A lead 14 is secured to the canister and includes sensing electrode A 16, coil electrode 18, and sensing electrode B 20. A can electrode 22 is shown on the canister 12. The subcutaneous system is provided generally between the ribcage and skin (neither of which is shown) of the patient. Several vectors for sensing are therefore available including A-can, B-can, and A-B. It should be noted that the use of the coil electrode 18 as a sensing electrode is also possible. Illustrative subcutaneous systems are shown in U.S. Pat. Nos. 6,647,292, 6,721,597 and 6,988,003. Some embodiments include a unitary system having two or more electrodes on a housing as set forth in the '292 and '003 patents, rather than that which is shown.

Referring now to FIG. 1B, a transvenous system is shown relative to a patient's heart 30. The transvenous cardiac stimulus system includes a canister 32 connected to a lead 34. The lead 34 enters the patient's heart and includes electrodes A 36 and B 38. Additional electrodes for sensing or stimulus delivery may also be included, and these may include coil electrodes as shown in FIG. 1A. In the illustrative example, electrode A 36 is located generally in the patient's ventricle, and electrode B 38 is located generally in the patient's atrium. The lead 34 may be anchored into the patient's myocardium. Again, a can electrode 40 is shown on the canister 32. With this system, plural sensing vectors may be defined as well. In both FIGS. 1A and 1B, one or more sensing electrodes may also be used for stimulus delivery. Some embodiments of the present invention may be used in a combination system having vectors defined between two subcutaneous electrodes, a subcutaneous electrode and a transvenous electrode, and two transvenous electrodes, with these vectors being available for detection and/or high and/or low energy stimulus delivery.

The systems shown in FIGS. 1A-1B may include operational circuitry and a power source housed within the respective canisters. Some illustrative examples are further explained by reference to FIG. 2, below. The power source may be, for example, a battery or bank of batteries. The operational circuitry may be configured to include such controllers, microcontrollers, logic devices, memory, and the like, as selected, needed, or desired for performing the illustrative methods set forth herein. The operational circuitry may further include a charging sub-circuit and a power storage sub-circuit (for example, a bank of capacitors) for building up a stored voltage for cardiac stimulus taking the form of cardioversion and/or defibrillation. The operational circuitry may be adapted to provide a pacing output. Both cardioversion/defibrillation and pacing sub-circuitry and capacities may be incorporated into a single device. In some embodiments, the methods discussed below are partly or wholly embodied in hardware within the operational circuitry and/or as instruction sets for operating the operational circuitry and/or in the form of machine-readable storage media (optical, electrical, magnetic, etc.) embodying such instructions and instruction sets, as well as combinations thereof.

Each of the devices 12, 32 may further include such components as would be appropriate for communication (such as RF communication or inductive telemetry) with an external device such as a programmer. To this end, programmers 24 (FIG. 1A) and 42 (FIG. 1B) are also shown. For example, once the implantable system is emplaced during implantation, the programmer 24, 42 may be used to activate the device and/or to direct/observe diagnostic or operational tests. Illustrative diagnostic tests include determinations of lead impedance and battery status, while illustrative operational tests may include observation of sensing data characteristics (amplitude and signal-to-noise ratio, for example), and, in some embodiments, testing to determine whether defibrillation can be successfully performed. After implant and activation, the programmer 24, 42 and the implanted devices 12, 32 may communicate with one another to allow interrogation and/or re-programming of the implanted device(s). The programmers 24, 42 in combination with the implanted devices 12, 32 may also allow annunciation of statistics, errors, history and potential problems to the user/physician.

The systems shown in FIGS. 1A-1B are merely illustrative. The present invention may be embodied in virtually any implantable cardiac stimulus system. For example, it may be embodied in transvenous or subcutaneous systems such as those shown in FIGS. 1A-1B, as well as hybrid systems combining features of both. Some embodiments may appear in intravascular systems modeled on those shown in US Patent Application Publication Number 2006/0224225 to Ransbury et al. In another example, the canister electrodes 22, 40 may form all or a substantial portion of the canister itself, rather than being placed as an isolated element separate from the canister 12, 32.

Figure 2:
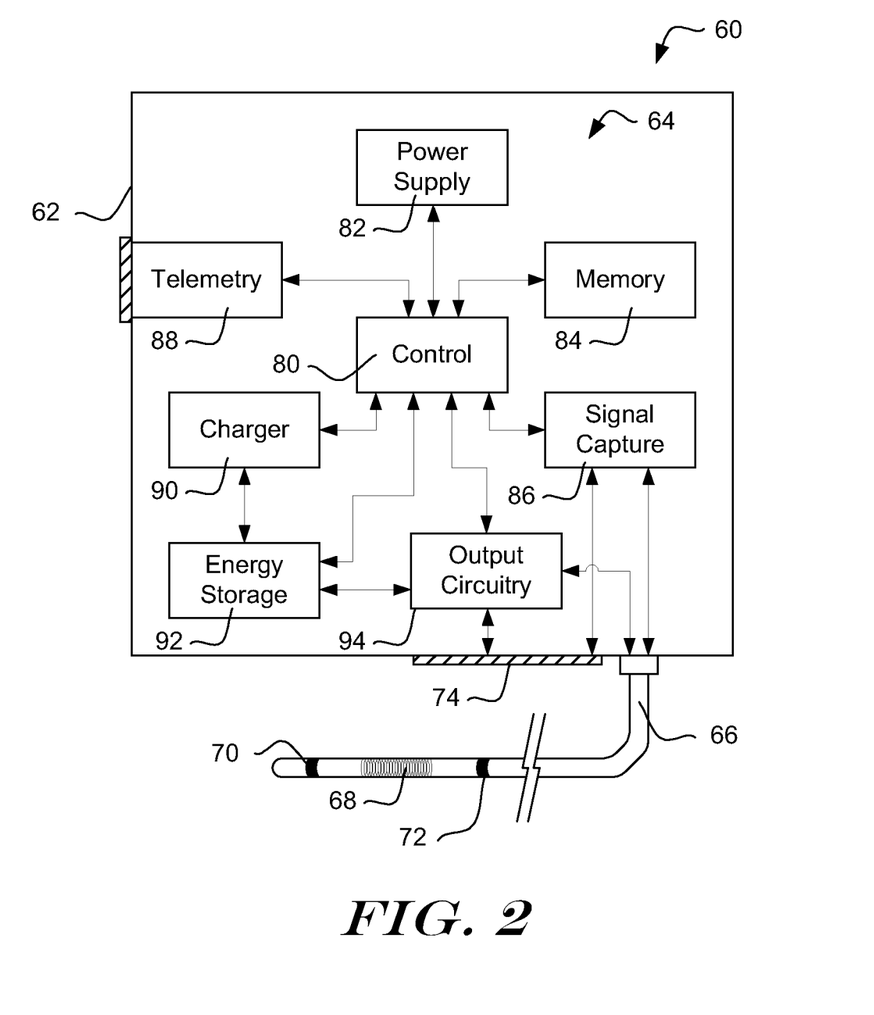
FIG. 2 is a functional block diagram for an implantable cardiac stimulus device.

FIG. 2 is a functional block diagram for an implantable cardiac stimulus device. The device 60 is housed within a canister 62, and includes operational circuitry shown at 64. A lead assembly 66 is coupled to the canister 62 at a first end thereof. The lead assembly 66 includes an elongate shaft having one or more electrodes 68, 70, 72 disposed along its second end. The number and form of the electrodes 68, 70, 72 may vary in other embodiments. In the example shown, a coil electrode is shown at 68, while ring electrodes are shown at 70 and 72. A can electrode 74 is shown on the canister 62. The electrodes 68, 70, 72, 74 may be used as shown in FIGS. 1A-1B, for example. The electrodes 68, 70, 72, 74 may be used or configured differently if desired, and one or more may be omitted, or other electrodes may also be added.

The operational circuitry 64 includes control block 80. In some examples, the control block 80 includes a microcontroller and/or suitable logic (such as flip flops, inverters, counters, registers, and/or other devices or sub-circuits providing greater complexity, for example) that enable mathematic or logical decisions to be made. Control block 80 is coupled to a number of other illustrative functional blocks. These include the power supply, shown at 82. The power supply 82 takes the form of one or more batteries, which may be of any suitable chemistry, capacity, number or form.

A memory block 84 is also shown and may take any suitable form (such as optical, magnetic, or electrical media) that can be read or queried by the control block 80. Memory block 84 may also include writable and read-writable components. A signal capture block 86 is also shown and may include suitable amplifiers and filtering components for receiving, filtering and amplifying an incoming signal. The signal capture block 86 and/or the control block 80 may also include analog-to-digital sub-circuitry for digitizing a signal captured from electrodes implanted in a patient. It should be noted that, unless otherwise noted herein, a "curve" refers to both a continuous value curve, and/or to an approximation of a continuous curve in discrete form; no limitation to one of these forms should be read into such terminology.

In some embodiments, the signal capture block 86 may include coupling circuitry having a plurality of switches, allowing selection of a pair of the plural electrodes (68, 70, 72, 74) by control block 80. Sensing vector selection may be performed in suitable fashion, for example, as set forth in copending U.S. patent application Ser. No. 10/901,258, now U.S. Pat. No. 7,392,085, and titled MULTIPLE ELECTRODE VECTORS FOR IMPLANTABLE CARDIAC TREATMENT DEVICES; U.S. patent application Ser. No. 11/441,522 published as US Patent Application Publication Number 2007-0276445, and titled SYSTEMS AND METHODS FOR SENSING VECTOR SELECTION IN AN IMPLANTABLE MEDICAL DEVICE; U.S. patent application Ser. No. 11/441,516, published as US Patent Application Publication Number 2007-0276447, and titled IMPLANTABLE MEDICAL DEVICES AND PROGRAMMERS ADAPTED FOR SENSING VECTOR SELECTION; U.S. patent application Ser. No. 11/442,228, published as US Patent Application Publication Number 2007-0276452, and titled IMPLANTABLE MEDICAL DEVICE SYSTEMS HAVING INITIALIZATION FUNCTIONS AND METHODS OF OPERATION; U.S. patent application Ser. No. 11/672,353 published as US Patent Application Publication Number 2008-0188901, and titled SENSING VECTOR SELECTION IN A CARDIAC STIMULUS DEVICE WITH POSTURAL ASSESSMENT; and/or U.S. patent application Ser. No. 11/623,472 published as US Patent Application Publication Number 2008-0172100, and titled SYSTEMS AND METHODS FOR SENSING VECTOR SELECTION IN AN IMPLANTABLE MEDICAL DEVICE USING A POLYNOMIAL APPROACH.

The operational circuitry 64 is also shown as including telemetry circuitry 88. The telemetry circuitry 88 can include any suitable devices/circuitry for use in sending and receiving signals. Telemetry circuitry 88 can be used to communicate with a programmer 24, 42 as shown in either of FIGS. 1A-1B.

During operation, the operational circuitry 64, including the control block 80, monitors signals captured using a pair (or more) of the electrodes 68, 70, 72, 74 to observe electric signals emanating from the heart of the patient. If it is determined that the patient needs stimulus, the control block 80 uses the charger 90 to store charge on the energy storage circuitry 92, which may include one or more capacitors. Control block 80 monitors the voltage/energy stored by energy storage 92 and, once a desired voltage/energy level is stored, the output circuitry 94 is used to deliver the stored energy to the patient using a pair (or more) of the electrodes. In some examples, the can electrode 74 and coil electrode 68 form a default electrode pair for stimulus delivery. Other pairings may be used in some embodiments, for example, in a transvenous embodiment, two lead electrodes (coils, rings, or other forms may be used) can be used to deliver a stimulus. The selection of an electrode pair for stimulus delivery may take any suitable form.

The implantable systems shown in FIGS. 1A-1B and 2, in an illustrative embodiment, make use of a sensing-detection method to identify cardiac events. Signals are captured using pairs or groups of electrodes during sensing. The sensed signals are analyzed by comparison to a detection threshold, which is a representation of amplitude. In the examples which follow, the detection threshold(s) are time varying thresholds. When the sensed signal meets or exceeds the amplitude represented by the detection threshold, a detected event is identified. In some embodiments, purely rate-based methods of arrhythmia detection are used, such that a calculated rate of detected events is compared to a threshold(s) to determine whether the patient is experiencing a malignant arrhythmia. In other embodiments, a rate is calculated using the detected events, and further analysis ensues when the rate exceeds a predetermined threshold, as set forth in a detailed example shown in FIG. 5. The further analysis may include morphology based analysis, for example.

Figure 3A:
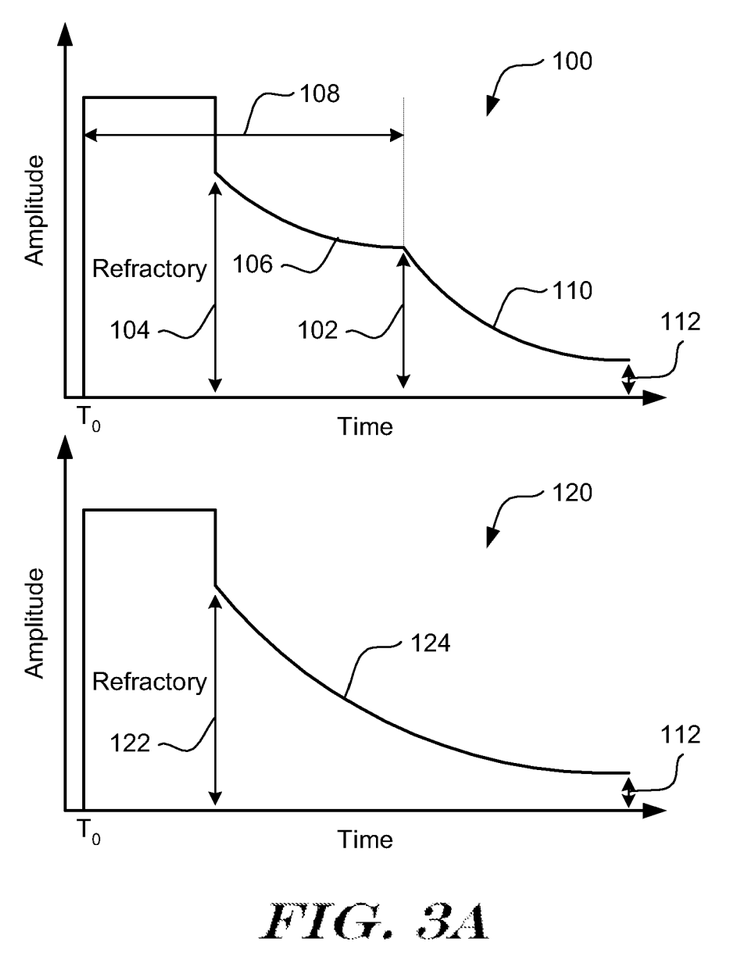
FIGS. 3A-3B compare illustrative dynamic and non-dynamic detection thresholds.

FIG. 3A compares illustrative dynamic and non-dynamic detection thresholds. The thresholds 100, 120 are differently shaped largely due to the inclusion of an intermediate decay target shown as dynamic target 102 in the dynamic detection threshold 100. The dynamic detection threshold 100 begins, following a refractory period after $T_0$, at a first value shown at 104 and decays along a first curve 106 to the dynamic target 102. $T_0$ represents the time of a previous threshold crossing that resulted in a detected event. The first value may be some predetermined percentage of one or more previous peak(s) amplitudes, or it may be predetermined value. When sufficient time passes, a dynamic timeout 108 expires, and the dynamic detection threshold 100 continues along a second curve 110 toward the ultimate sensing floor 112.

The value for the dynamic target 102 may be, for example, some percentage of a previous peak amplitude in a detected event, or an average of previous peaks from detected events, or it may be a predetermined value. The dynamic target 102 may also vary in response to other detected conditions.

The timeout 108 may take a suitable form as well, for example, timeout 108 may be a set period of time. The duration of the timeout 108 may be a user adjustable parameter. For example, during implantation or during a check-up, an administering technician or physician may determine an appropriate value for the timeout 108. An illustrative value could be a duration that is longer than observed Q-T intervals for the patient, such that the dynamic target 102 can avoid erroneous detection of both Q and T waves from the same cardiac event. In another example, a patient having a relatively wide QRS complex may receive a device, and the dynamic timeout 102 may be selected to avoid erroneous detection of the trailing edge of the QRS complex by allowing the dynamic target 102 to pass over the trailing edge of the QRS complex. The timeout 108 may also vary in response to detected conditions or cardiac status, for example.

Typically the ultimate sensing floor 112 will be defined as the noise floor of the system, that is, a level at or near some percentage of the average background noise, and/or the ultimate sensing floor 112 may be set to the lowest unit available for detection. For example, a captured cardiac signal may undergo analog-to-digital conversion, and the ultimate sensing floor may be set to one digital unit or some higher level, if desired. In another illustrative example, the ultimate sensing floor 112 is about 80 µV, though this value may vary depending upon system capabilities, electrode placement, and environmental noise, among other factors.

Figure 3B:
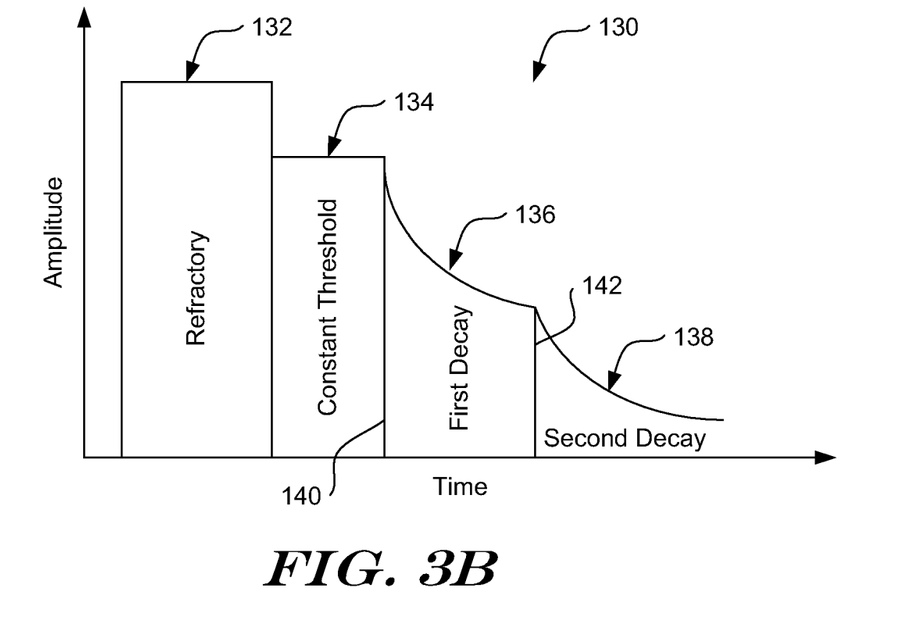

In contrast to the dynamic detection threshold 100, the non-dynamic detection threshold 120 begins, following the refractory period after $T_0$, at a first value shown at 122 and decays along a single curve 124 to the ultimate sensing floor 112. The first values 104, 122 may be generated in several ways including, for example, as set values, as percentages of one or more previously detected event peaks, and as variables related to rate or other factors. While exponential decays are shown in FIG. 3A-3B, these may be replaced, if desired, with functions approximating a line. Alternatively, the dynamic detection threshold 100 may include one or more additional intermediate points in addition to the dynamic target 102, with associated timeouts.

In an illustrative embodiment, the dynamic detection threshold 100 is used during time periods where the operational circuitry estimates a cardiac event rate in a benign range. The detected event rate, in this example, is assumed by the operational circuitry to represent "beat rate." The benign range may be, for example, in a range of 40-170 events-per-minute, though this range is merely illustrative. One illustrative example uses 100 events-per-minute. The benign range may be non-arrhythmic, that is, neither tachyarrhythmic nor bradyarrhythmic, and those of skill in the art will recognize that the boundaries of such ranges are imprecise and will vary from patient to patient. In the same illustrative embodiment, the non-dynamic detection threshold 120 is used when the operational circuitry estimates a cardiac event rate that is tachyarrhythmic.

In an illustrative embodiment, the non-dynamic detection threshold 120 is used in combination with enhanced analysis of cardiac signal. For example, additional consideration is given in some embodiments to identifying individual events as malignant or non-malignant on the basis of individual event morphology as set forth in copending and commonly assigned U.S. patent application Ser. No. 10/856,084, now U.S. Pat. No. 7,330,757, and titled METHOD FOR DISCRIMINATING BETWEEN VENTRICULAR AND SUPRAVENTRICULAR ARRHYTHMIAS. An X/Y counter (where a set of Y chosen detected events is monitored to determine whether at least X of the Y events is considered malignant by the ongoing event analysis) may be used taking into account morphology and/or period/frequency of detected events. Other forms of enhanced operation may be used as well including, for example, those shown in U.S. Provisional Patent Application No. 61/051,332, titled METHODS AND DEVICES FOR IDENTIFYING AND CORRECTING OVERDETECTION OF CARDIAC EVENTS.

The dynamic detection threshold 100, because it includes the dynamic target 102, is more likely to avoid early detection of noise following a cardiac event, for example, passing over T-waves or avoiding the trailing edge of wide QRS complexes. When the dynamic detection threshold 100 is used while detected event rates are in a benign (low) range, it may not be necessary to expend additional computational effort (and energy) on enhanced analysis. If the detected event rate rises out of this "benign" range, the non-dynamic detection threshold 100 may be used, and "enhanced" analysis or other factors are then relied upon to avoid erroneous detection and resultant miscounting of cardiac events. Some examples are set forth below.

FIG. 3B shows an alternative to the dynamic detection threshold shown at 100 in FIG. 3A. In this illustrative example, the detection threshold includes a refractory period 132, during which a new detected event cannot occur, a constant threshold period 134 during which a relatively high detection threshold, in terms of the estimated peak, is applied. Next a first decay 136 is shown, followed by a second decay 138. The first decay begins at a first timeout 140, and the second decay begins at a second timeout 142. These additional settings allow for further event detection control. Further examples are shown in U.S. Provisional Patent Application No. 61/034,938, titled ACCURATE CARDIAC EVENT DETECTION IN AN IMPLANTABLE CARDIAC STIMULUS DEVICE.

Figure 4A:
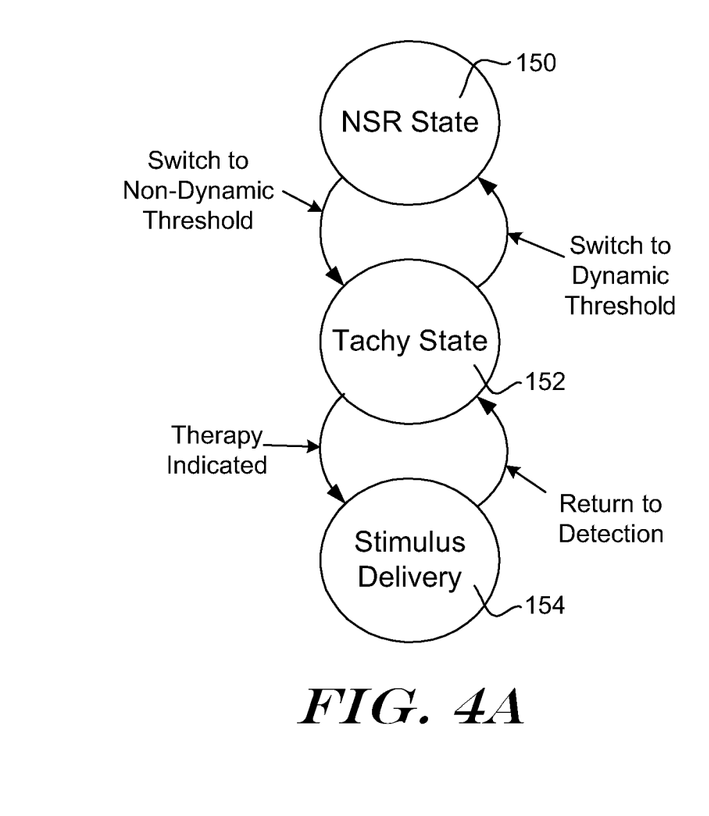
FIGS. 4A-4B are state diagrams for illustrative cardiac stimulus systems.
Figure 4B:
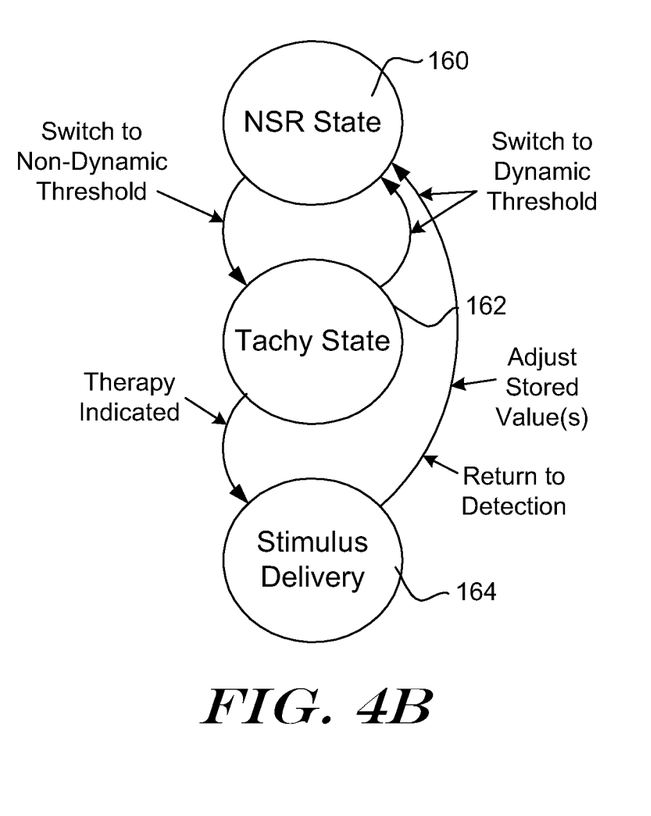

FIGS. 4A-4B are state diagrams for illustrative cardiac stimulus systems. FIG. 4A shows a first example. An NSR State 150 is defined. "NSR" typically stands for normal sinus rhythm, however, the term is used herein more generally as shorthand for a non-malignant cardiac condition and/or for relatively lower rate conditions; that the patient has clinically "normal" or "sinus" rhythm is not required. In the illustrative example, the NSR State 150 occurs while the rate of detected events is below a first threshold. The first threshold may be, for example, in the range of 150-240 events-per-minute. In an illustrative example, the first threshold is about 200 events-per-minute; the first threshold may be a variable selected by a physician from a range. Also in an illustrative example, the NSR state 150 is one in which a Dynamic threshold (FIG. 3A, 100 or FIG. 3B) is used for purposes of event detection. The NSR State 150 is exited if and when the detected event rate exceeds the first threshold. Upon exit of the NSR State 150, the system may switch to a Non-Dynamic threshold (FIG. 3A at 120), as indicated.

A Tachy State 152 is also defined. The Tachy State 152 arises when the NSR State 150 is exited due to an event rate in excess of the first threshold. The Tachy State 152 gives rise to additional analysis of detected events for the purpose of at least one of: certifying that detected events appear to be actual cardiac events, rather than overdetections (multiple detected events occurring due to signals from a single cardiac event) or erroneous detections occurring due to noise, and/or determining that the events giving rise to the high detected event rate are themselves malignant. For example, some recipients of implantable cardiac stimulus devices may be able to safely engage in physical exertion that would give rise to an elevated detected event rate, yet those same patients may also be susceptible to sudden cardiac death. If detected high-rate events are regular in periodicity, amplitude, and/or morphology, an illustrative ICSD may determine that a patient does not need cardiac stimulus, although the elevated rate may call for added scrutiny.

In another example, some detected events may be identified as resulting from incorrect detections, for example, if a large T-wave or the trailing edge of a wide QRS complex is detected in addition to the R-wave of the same event, the resultant event rate be twice or even three times the actual beat rate. Identification of over-detection can also prevent erroneous application of stimulus, using methods as in U.S. Provisional Patent Application No. 61/051,332, titled METHODS AND DEVICES FOR IDENTIFYING AND CORRECTING OVERDETECTION OF CARDIAC EVENTS. Thus, for example, detected events may be categorized as: malignant, non-malignant, or non-cardiac event.

In the illustrative state of FIG. 4A, the Tachy State 152 may be exited in one of two ways. First, it may be determined that the event rate has dropped below a second threshold, and the system returns to the NSR State 150. In some embodiments, hysteresis may be built into the system, for example, by requiring expiration of a timer before allowing changes between states 150, 152, or by using different thresholds to determine whether to change states. In an illustrative example, the first threshold is 200 events-per-minute, while the second threshold is 180 events-per-minute.

Upon transition from the Tachy State 152 to the NSR State 150, the system may switch to a Dynamic Threshold, as indicated. The Tachy State 152 may also be exited by determining that therapy is indicated, in which case the device goes to a Stimulus Delivery State 154.

In the Stimulus Delivery State, preparations are made for delivering a cardiac stimulus and the cardiac stimulus may be delivered. For example, a capacitor in the implanted device may be charged to a stimulus voltage/energy, and input/output circuitry manipulated to effect stimulus delivery. In some embodiments, conditions indicating therapy are re-checked just prior to delivering stimulus in Stimulus Delivery State 154. If conditions change such that stimulus is no longer indicated, the system exits the Stimulus Delivery State 154. If stimulus is delivered, the Stimulus Delivery State 154 is exited, and any data stored in the system typically continues to qualify for the Tachy State 152. Thus, as shown, the return to detection from Stimulus Delivery 154 goes to the Tachy State 152. When stimulus is delivered, the registers used to count events (for example, an X/Y register) may be filled with data indicating that stimulus is necessary. In order to prevent unnecessary and possibly harmful additional stimuli, it may be desirable to replace some of this stored data, as shown in the embodiment of FIG. 4B.

In another illustrative embodiment, stimulus delivery is followed by a temporary sensing state that uses a sensing vector different than the default sensing vector. For example, in the subcutaneous-only ICD shown in FIG. 1A, stimulus can be applied between the canister electrode 22 and the coil electrode 18 on the lead. Following stimulus delivery, a residual voltage difference may persist between the region of the coil electrode 18 and the canister 12, and this voltage may make detection using combinations A-Can and B-Can difficult. Therefore, during a time period following the stimulus delivery, the detection method may switch (if not already using vector A-B) to the A-B vector for detection. Such methods may also be used in conjunction with post-shock filtering such as that shown in U.S. patent application Ser. No. 11/497,204 published as US Patent Application Publication Number 2008-0045850, and titled HEURISTIC FILTER FOR CARDIAC EVENT DETECTION. Additional methods and devices configured to help with post shock sensing are shown in U.S. Provisional Patent Application No. 61/122,327, titled IMPLANTABLE DEFIBRILLATOR SYSTEMS AND METHODS WITH MITIGATIONS FOR SATURATION AVOIDANCE AND ACCOMMODATION. Post-shock bradycardia pacing may also be provided, if desired.

FIG. 4B also includes the NSR State 160, Tachy State 162, and Stimulus Delivery State 164, which may be similar to those shown in FIG. 4A. However, the steps occurring at transitions of these states are different. In particular, the return to detection from the Stimulus Delivery State 164 is shown as including an Adjust Stored Values step. This causes a return to the NSR state 160, and, optionally, a switch to the dynamic threshold, as shown. For example, event rate/interval information may be modified or replaced with information causing predictable return to a desired state. In the illustrative example, the NSR state 160 is activated following stimulus delivery 164. In addition to rate/interval and/or timing data, other data may be modified. For example, data used to define amplitudes in a detection profile may be modified.

Figure 5:
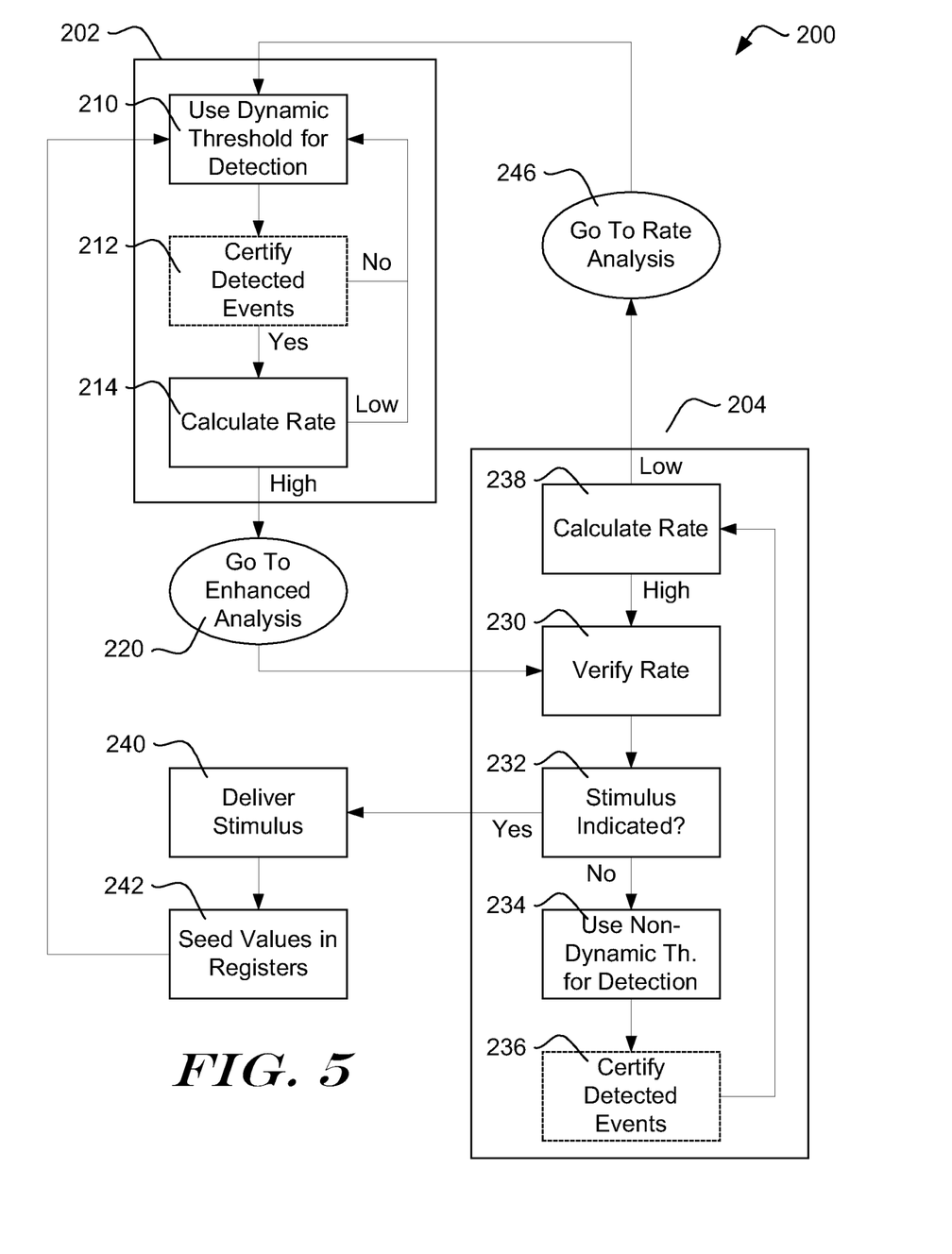
FIG. 5 is a process flow block diagram for an illustrative example.

FIG. 5 is a process flow block diagram for an illustrative example. A method 200 is shown as including a Rate Analysis Loop 202 and Enhanced Analysis loop 204. Rate Analysis Loop 202 uses a dynamic threshold for detection, as indicated at 210. The method stays at block 210 until a sensed signal exceeds the dynamic threshold. Next an optional step 212 in which detected events are certified is performed. This may include preliminary analysis of a detected event using methods such as in U.S. patent application Ser. No. 10/858,598, now U.S. Pat. No. 7,248,921, and titled METHOD AND DEVICES FOR PERFORMING CARDIAC WAVEFORM APPRAISAL. If the detected event(s) is not certified at step 212, associated data is discarded and the method returns to step 210 and waits for a next detected event.

If the detected event(s) is certified at step 212, the method continues to step 214, where the event rate is calculated. In an illustrative embodiment, event rate is calculated by recording event intervals between previously detected events. If certification at 212 is performed, the event rate may be calculated by recording event intervals between certified detected events. For example, N timestamps may be recorded for a previous N consecutive detected events, as long as no non-certified events intervene, and the rate can be calculated as the inverse of the average period. Rather than timestamps, intervals between certified events may be recorded. In one example, four (or more or less) intervals are retained in a first-in first-out buffer. In some embodiments, step 212 is skipped and the method proceeds directly to step 214.

The rate calculated at step 214 is then compared to a threshold, and it is determined to be either "Low," in which case the method returns to step 210 and waits for a next detection, or the rate may be "High" and the method then goes to Enhanced Analysis as shown at 220. The determination of Low/High may use thresholds as before.

The Enhanced Analysis Loop 204 is entered at block 230, where a rate is verified. A rate may be verified by analyzing a set of detected events to determine whether over-detection is occurring, for example. In general, these steps may be performed in any suitable order. Rate verification 230 may include consideration of non-rate based factors to determine whether one or more detected events should be discarded due to identified over-detection. If data is discarded by rate verification 230, the method may include re-calculating the detected rate by returning to step 238, for example, or by simply performing a rate re-calculation within block 230.

Next it is determined whether stimulus is indicated, as shown at 232. In the illustrative example, the method 200 requires switching from one loop 202 to the other loop 204 before a stimulus indication can occur. If stimulus is not indicated at step 232, a non-dynamic threshold is used for detection as shown at 234. Again, an optional step of certifying detected events is shown at 236, before rate calculation is performed at 238. After rate calculation 238, a determination is made as to whether the rate is High or Low. Based on this determination, the method 200 either stays in loop 204 by returning to rate verification 230, or the method 200 goes to the other loop 202.

The step of determining whether stimulus is indicated 232 may include one or more of several calculations. Persistence of a detected high rate in excess of a fibrillation/tachyarrhythmia threshold may be observed. Morphology comparisons may also be performed, such as those as set forth in U.S. patent application Ser. No. 10/856,084, Now U.S. Pat. No. 7,330,757, and titled METHOD FOR DISCRIMINATING BETWEEN VENTRICULAR AND SUPRAVENTRICULAR ARRHYTHMIAS. Additional explanation of some illustrative methods may be found in U.S. patent application Ser. No. 11/042,911, published as US Patent Application Publication Number 2006-0167503, and titled METHOD FOR ADAPTING CHARGE INITIATION FOR AN IMPLANTABLE CARDIOVERTER-DEFIBRILLATOR.

Once it is determined that stimulus is indicated at step 232, the method exits the Enhanced Analysis Loop 204 and goes to block 240 for stimulus delivery. This may include continued monitoring of electrical cardiac signals to assure persistence of the conditions that led to a determination that stimulus was indicated at block 232. If some act of stimulus fails, for example, the detected rate drops due to the patient returning to a non-malignant cardiac state, the system may revert to the Rate Analysis Loop 202. Stimulus delivery 240 can also include observing detection features in order to synchronize stimulus delivery. Stimulus can then be delivered when appropriate conditions are found.

After stimulus delivery, the method 200 seeds values in one or more registers or other data structures or memory in the operational circuitry as indicated at block 242. Seeding values may include storing an amplitude value for previous peak amplitude(s). Seeding values 242, in another illustrative embodiment, includes seeding timing and/or interval data. In an illustrative example, seeding is performed to cause the device to identify a benign cardiac event rate in the range of 40-140 bpm. Seeding of the rate values may also cause the device to automatically invoke a different threshold, for example, switching from threshold 120 in FIG. 3A to threshold 130 in FIG. 3B.

In an illustrative example, data is seeded to cause the analysis in a rate calculation block, such as blocks 214 or 230, to determine a cardiac event rate of 100 bpm. With the seeded data, the method 200 returns to the Rate Analysis Loop 202, going to block 210 and awaiting a next event detection using the dynamic threshold. When additional cardiac events are detected, the seeded data is included in calculations of event rate. In an illustrative example, a plurality of stored event intervals are used to calculate event rate in step 214, and as new data is captured, the seeded data is replaced by actual event data.

In another illustrative example, peak amplitude data is seeded such that, following conversion, the threshold (be it dynamic or non-dynamic) used for comparison to captured signal to detect events is artificially raised using the seeded value. For example, prior to stimulus delivery, the amplitude of a tachyarrhythmia is typically much lower than the patient will experience during a benign sinus rhythm. By seeding data, the threshold for detection can be raised to avoid over-detecting noise in the event that stimulus delivery results in successful conversion of an arrhythmia. In an illustrative example, two or more prior (non-tachyarrhythmic) detected event amplitudes are used to establish values used in a time-decaying threshold as shown in FIG. 3, and these values are replaced as new events are detected. The seeded amplitude data may be used at least until it is eliminated from the data structure storing such event data.

In a further illustrative example one or more additional factors may be considered before either of steps 220 or 246 is invoked. For example, after switching between loops 202, 204, the method may also set a counter that prevents switching states again for at least a predetermined period of time and/or a predetermined number of detected events. As noted before, the determinations of High/Low may be performed using different thresholds in each of the loops 202, 204 in order to create a hysteresis effect and prevent switching between loops 202, 204.

One or more additional intervening steps may be performed before seeding of values at step 242. In an illustrative example, following stimulus delivery at step 240, bradycardia pacing may be performed, though this is not shown. Alternatively, bradycardia pacing may be performed on top of the analysis in Rate Analysis Loop 202.

By placing the device into a low-rate state, the seeding of data delays additional delivery of stimulus. Such delay does not need to be very long, however, as the patient who continues to experience a tachyarrhythmia following stimulus delivery will relatively quickly refill data registers related to rate. In addition, the seeding of data can prevent overdetection of noise following stimulus delivery that can otherwise happen if pre-stimulus sensing parameters continue to be used.

For example, following shock delivery, an ICSD which does not seed data after stimulus may erroneously detect artifacts or noise without adequately capturing a normal sinus signal, which may be missed due to the combination of early detection (i.e. a large P-wave) and short refractory. False detection may occur due to failure to change sensing parameters. If stored rate data is not changed, the false detection can result in a quick determination that an arrhythmia is occurring and subsequent initiation of charging of the energy storage circuitry. In some such instances, a stimulus will be erroneously delivered. In other circumstances, a re-check of rate/rhythm prior to shock delivery may prevent erroneous stimulus delivery, though unnecessary waste of limited energy resources would still occur.

Figure 6A:
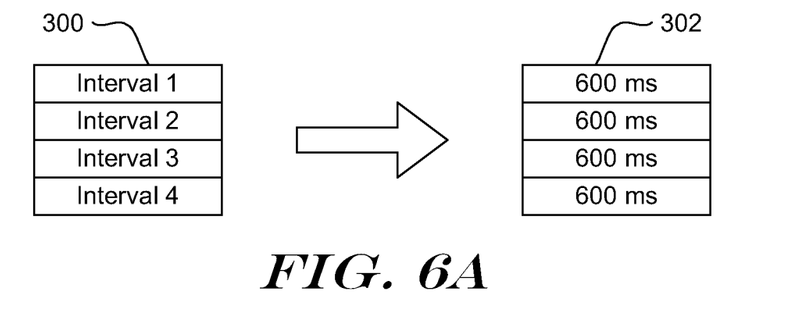
FIGS. 6A-6C illustrates data manipulation in an illustrative example.
Figure 6B:
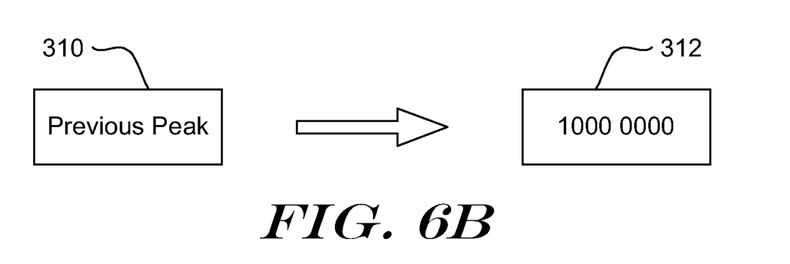
Figure 6C:
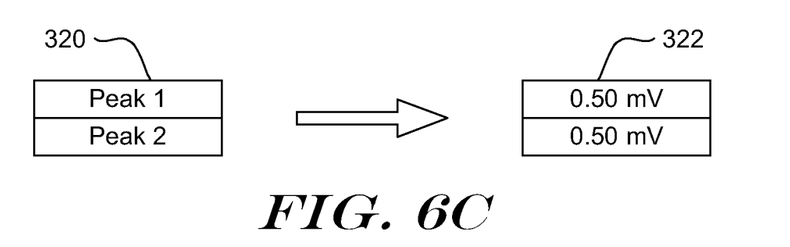

FIGS. 6A-6C provide examples of data manipulation that can be part of a data seeding operation. In FIG. 6A, as shown at 300, a plurality of intervals are stored, for example in a memory structure. A transformation is performed to replace these stored intervals with new data. In the illustrative example, the new data indicates intervals of 600 ms, as shown at 302, which corresponds to an event rate of 100 events-per-minute. In FIG. 6B, a byte of data is used to store a previous peak amplitude, as shown at 310. In the illustrative transformation, the data is replaced as shown at 312 by the byte [1000 0000] which, for an unsigned byte of data, is in the middle of the available range. In FIG. 6C, two previous peak values are stored as shown at 320 and these are replaced with values as shown at 322 of 0.5 millivolts.

The examples of FIGS. 6A-6C are merely illustrative. Different values may be seeded. In one illustrative example, data manipulation may be performed by taking into account the dynamic range of the device. In an illustrative example, a device may use more than one selectable input amplification mode (i.e. a wide dynamic input range and a narrow dynamic input range), and the seeded values may vary depending upon which input range is in use. Combinations of these data manipulations may be performed as well.

Figure 7:
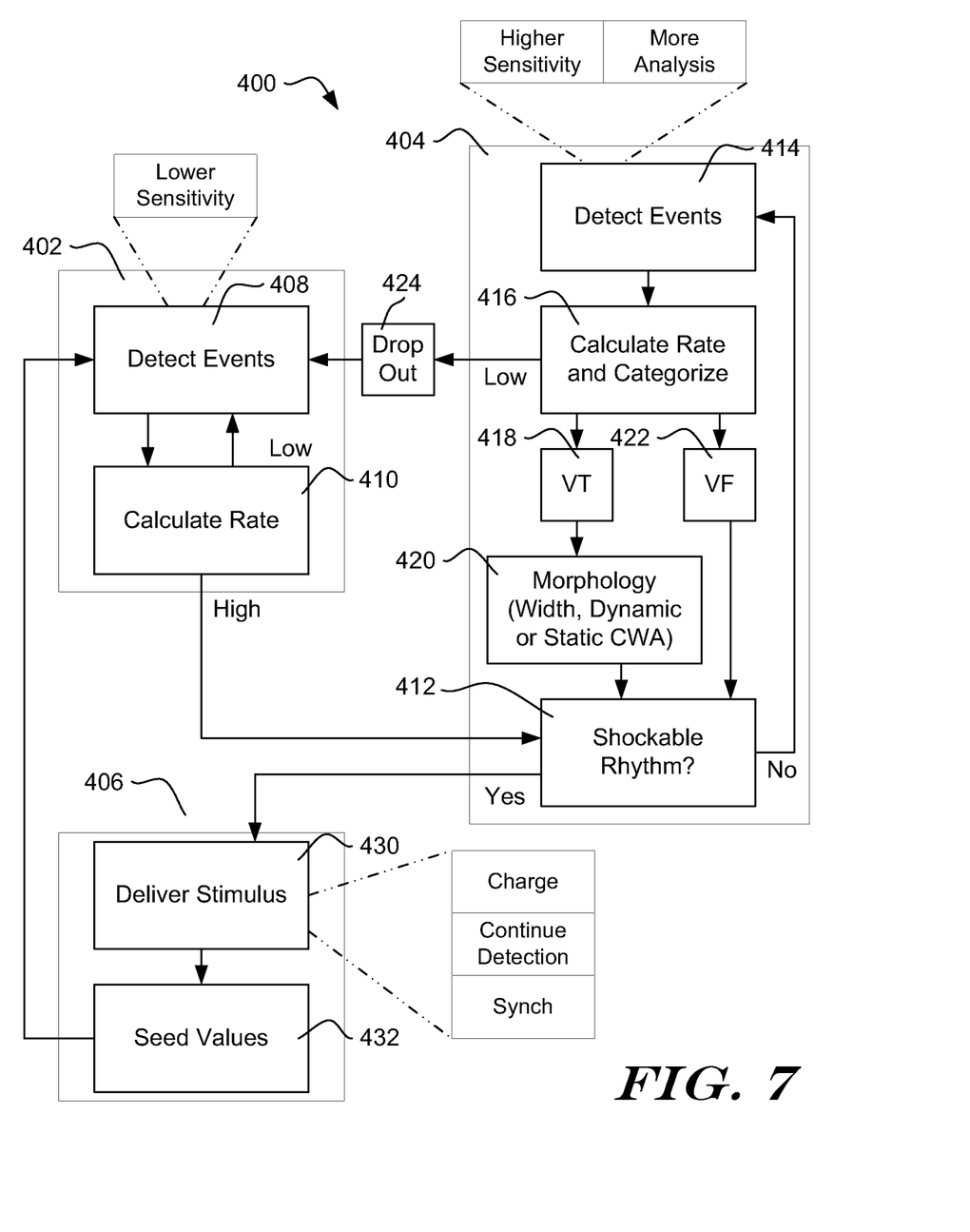
FIG. 7 is a process flow block diagram for another illustrative example.

FIG. 7 is a process flow block diagram for another illustrative example. In the illustrative method 400, rate analysis block 402, enhanced analysis block 404, and stimulus block 406 are used. During rate analysis, events are detected at 408, and rate is calculated at 410. Block 408 uses a dynamic detection profile as shown in FIG. 3A or FIG. 3B. Rate calculation block 410 may use, for example, an average interval calculation across several detected events. If desired, double detection identification and elimination may be used in block 402, such as the methods shown in U.S. Provisional Patent Application No. 61/051,332, titled METHODS AND DEVICES FOR IDENTIFYING AND CORRECTING OVERDETECTION OF CARDIAC EVENTS. Further, the dynamic profile may be adjusted on a beat-to-beat basis using amplitude similarity/dissimilarity as in some embodiments disclosed in U.S. Provisional Patent Application No. 61/034,938, titled ACCURATE CARDIAC EVENT DETECTION IN AN IMPLANTABLE CARDIAC STIMULUS DEVICE.

The rate calculation step at 410 may be used to identify high rates using a tachyarrhythmia classification set at a predetermined value, for example, 140-200 bpm. When a tachyarrhythmia rate is identified, the method goes to the enhanced analysis block 404. In the example shown, the transition goes to a shockable rhythm block 412 and begins to iterate within the enhanced analysis block 404. In the enhanced analysis block, detected events are captured at 414 using a non-dynamic detection profile as shown at 120 in FIG. 3A. The cardiac rate is then calculated and categorized, as shown at 416, as one of ventricular tachycardia (VT) 418 or ventricular fibrillation (VF) 422. A third category of non-VT (not shown) may accommodate rates below a VT threshold but sufficiently high to avoid drop out 424. In an illustrative example, drop out 424 occurs when a predetermined number of consecutive rate calculations are below another predetermined drop-out threshold.

Following rate calculation and categorization at 416, if a VT rate 418 is found, enhanced analysis including, for example, QRS width estimation, and dynamic or static correlation waveform analysis is performed, as shown at 420. The outcome of block 420 is to determine whether a given detected event is shockable or not. Alternatively, if a VF rate 422 is found at step 416, the detected event is marked as shockable without morphology analysis at 420. In an illustrative example, multiple rate zones can be identified to distinguish VT 418 from VF. For example, across a range from 180-240 bpm, a VT/VF threshold may be set such that rates above the VT/VF threshold are considered VF 422, and rates at or below the VT/VF threshold but above a VT lower threshold (set illustratively at 180 bpm) are considered VT 418. Thus, if the VT/VF threshold is set to 210 bpm, a rate over 210 bpm would be considered VF 422, and rates up to 210 bpm would be considered VT 418.

As the method iterates, a window of detected events is captured. The determination of shockable rhythm 412 uses the window of detected events to determine whether an X/Y buffer is filled with a sufficient number of shockable beats. For example, an 18/24 threshold may be used. A persistence factor may be used in step 412 as well, for example, requiring the X/Y threshold to be met for N consecutive events, where N is a set integer. In another embodiment, the persistence factor N may vary in response to prior terminations of shockable conditions, as shown in U.S. patent application Ser. No. 11/042,911 published as US Patent Application Publication Number 2006-0167503, and titled METHOD FOR ADAPTING CHARGE INITIATION FOR AN IMPLANTABLE CARDIOVERTER-DEFIBRILLATOR.

If a shockable rhythm is found at 412, the method goes to the stimulus block 406. Here, stimulus is delivered, as shown at 430, following a stimulus delivery protocol. For example, continued rhythm analysis may occur while a power capacitor is charged to a stimulus voltage. Dropout conditions 424 may be applied, though the link to block 424 is not shown. For example, if the observed rate drops to a normal range, stimulus delivery may be aborted. Stimulus delivery 430 may be synchronized or not, as desired. Following stimulus delivery 430, if it occurs, values are seeded, as shown at 432. This may include the methods noted above with reference to FIGS. 6A-6C. Seeding values 432 may include, for example, replacing captured rate information or captured signal amplitude information with a predetermined set of values. As noted above, this can result in selection of a different detection profile than may otherwise be selected, or may alter the detection profile that will be applied to detect subsequent cardiac events. The method then returns to rate analysis block 402.

In another illustrative example, the step of seeding values may be invoked following other deliveries of electrical pulses. For example, induction is a process designed to cause a patient to enter a malignant cardiac state. Induction is typically performed to test device sensing and stimulus delivery capabilities as an adjunct to implantation of a new device. In an illustrative example, when induction is called, new data values are seeded in the device to ensure desired operation. For example, data values may be seeded to ensure that the device follows induction with some set of default parameters, in order to ensure that the previous state of the device prior to induction will not affect device performance. The default parameters may include setting a relatively high estimated peak and relatively low rate data.

Those skilled in the art will recognize that the present invention may be manifested in a variety of forms other than the specific embodiments described and contemplated herein. Accordingly, departures in form and detail may be made without departing from the scope and spirit of the present invention as described in the appended claims.

What is claimed is:

1. A method of cardiac signal analysis in an implantable cardiac stimulus device (ICSD) having electrodes adapted for implantation into a patient's body and operational circuitry contained in a housing coupled to the electrodes, the method comprising:
   the ICSD delivering cardiac stimulus;
   following the delivery of stimulus, the operational circuitry capturing a cardiac signal from the electrodes;
   the operational circuitry identifying a cardiac event in the captured cardiac signal by comparing the captured cardiac signal to an amplitude threshold, the amplitude threshold being defined:
      by a first shape when the ICSD is in a first state; and
      by a second shape different from the first shape when the ICSD is in a second state; and
   wherein:
   when in the second state, the ICSD can determine that cardiac stimulus is indicated;
   when in the first state, the ICSD cannot determine that cardiac stimulus is indicated;
   the ICSD is configured to automatically set itself to the first state without reference to the captured cardiac signal following the delivery of cardiac stimulus and detect at least one detected event while in the first state; and
   the method further comprises the operational circuitry storing data related to the detected event including a rate calculation, and wherein the operational circuitry is also configured to modify at least some rate calculation data in the stored data following delivery of a cardiac stimulus, without reference to the captured cardiac signal.

2. The method of claim 1 wherein the patient's cardiac rate is used in determining which of the first state and the second state the ICSD should use, with the first state being used when the patient's cardiac rate is at relatively lower levels and the second state being used when the patient's cardiac rate is at relatively higher levels.

3. The method of claim 1 wherein the operational circuitry is configured such that the detected event is intended to represent a single cardiac cycle.

4. An implantable cardiac stimulus device (ICSD) comprising operational circuitry coupled to a plurality of electrodes such that: the operational circuitry can capture cardiac event data using a selected plurality of at least two electrodes when the ICSD is implanted in a patient; and the operational circuitry can deliver cardiac stimulus to a patient using a selected plurality of at least two electrodes when the ICSD is implanted in the patient;
   wherein the operational circuitry is configured to identify a cardiac event in a captured cardiac signal by comparing the captured cardiac signal to an amplitude threshold, the amplitude threshold being defined:
      by a first shape when the ICSD is in a first state; and
      by a second shape different from the first shape when the ICSD is in a second state;
   wherein the ICSD is configured to deliver stimulus to a patient and, following the delivery of stimulus, the operational circuitry is configured to automatically set the ICSD to the first state without reference to the captured cardiac signal and detect at least one detected event while in the first state;
   wherein when in the second state, the operational circuitry is enabled to determine that cardiac stimulus is indicated and, when in the first state, the operational circuitry is not enabled to determine that cardiac stimulus is indicated;
   wherein the operational circuitry is further configured to store data related to the detected event includes modifying a rate calculation, and
   wherein the ICSD is also configured to modify at least some rate calculation data in the stored data following delivery of a cardiac stimulus, without reference to the captured cardiac signal.

5. The ICSD of claim 4 wherein the operational circuitry is configured to use the patient's cardiac rate to determine which of the first state and the second state the ICSD should use, with the first state being used when the patient's cardiac rate is at relatively lower levels and the second state being used when the patient's cardiac rate is at relatively higher levels.

6. The method of claim 4 wherein the operational circuitry is configured such that the detected event is intended to represent a single cardiac cycle.

7. An implantable cardiac stimulus device (ICSD) comprising analysis means for analyzing data coupled to sensing means for sensing cardiac electrical signals;
   wherein the analysis means is configured to identify a cardiac event in a sensed cardiac electrical signal by comparing the sensed cardiac electrical signal to an amplitude threshold, the amplitude threshold being defined:
      by a first shape when the ICSD is in a first state; and
      by a second shape different from the first shape when the ICSD is in a second state; and
   wherein the ICSD is configured to deliver stimulus to a patient and, following the delivery of stimulus, the analysis means is configured to automatically set the ICSD to the first state without reference to the captured cardiac signal and identify at least one cardiac event while in the first state;

wherein, when in the second state, the analysis means is enabled to determine that cardiac stimulus is indicated and, when in the first state, the analysis means is not enabled to determine that cardiac stimulus is indicated; further wherein:

the analysis means is further configured to store data related to the identified cardiac events and calculate and store a cardiac rate therefrom;

the analysis means is further configured to modify at least one stored cardiac rate following the delivery of a cardiac stimulus, without reference to the sensed cardiac electrical signal.

8. The ICSD of claim 7 wherein the analysis means is configured to use the patient's cardiac rate to determine which of the first state and the second state the ICSD should use, with the first state being used when the patient's cardiac rate is at relatively lower levels and the second state being used when the patient's cardiac rate is at relatively higher levels.

9. The ICSD of claim 7 wherein the analysis means is configured such that the detected event is intended to represent a single cardiac cycle.

* * * * *